(12) United States Patent
Ito et al.

(10) Patent No.: US 8,202,326 B2
(45) Date of Patent: Jun. 19, 2012

(54) HAIR DYE COMPOSITION, OXIDATION HAIR DYE COMPOSITION AND METHOD FOR PREVENTION OF CHANGE IN COLOR TONE OF HAIR DYEING

(75) Inventors: Masao Ito, Aichi-gun (JP); Hisohisa Murakoshi, Aichi-gun (JP); Junji Yamagata, Aichi-gun (JP)

(73) Assignee: Hoyu Co., Ltd., Aichi (JP)

( * ) Notice: Subject to any disclaimer, the term of this patent is extended or adjusted under 35 U.S.C. 154(b) by 0 days.

(21) Appl. No.: 13/145,021

(22) PCT Filed: Jan. 26, 2009

(86) PCT No.: PCT/JP2009/051675
§ 371 (c)(1),
(2), (4) Date: Jul. 18, 2011

(87) PCT Pub. No.: WO2010/084625
PCT Pub. Date: Jul. 29, 2010

(65) Prior Publication Data
US 2011/0271466 A1 Nov. 10, 2011

(51) Int. Cl.
*A61Q 5/10* (2006.01)

(52) U.S. Cl. ............. 8/405; 8/406; 8/410; 8/411; 8/435; 8/587

(58) Field of Classification Search ............... 8/405, 406, 8/410, 411, 435, 587
See application file for complete search history.

(56) References Cited

FOREIGN PATENT DOCUMENTS

| DE | 10 2004 060 224 | 6/2006 |
|---|---|---|
| JP | 2002-201117 | 7/2002 |
| JP | 2005-041820 | 2/2005 |
| JP | 2007-008892 | 1/2007 |
| WO | WO-95/34272 | 12/1995 |
| WO | WO-2008/151858 | 12/2008 |

OTHER PUBLICATIONS

English abstract of the Japanese Patent # 2005041820 dated Feb. 17, 2005.*

* cited by examiner

*Primary Examiner* — Eisa Elhilo
(74) *Attorney, Agent, or Firm* — Jordan and Hamburg LLP

(57) ABSTRACT

A hair dye composition containing an organic compound having not more than 4 carbon atoms, which has both of a —SH group and a —NH$_2$ group and does not have a —COOH group, and also containing at least one member selected from aromatic compounds in which given substituents are each attached to meta positions of a mononuclear benzene ring structure and α-naphthol as a coupler of an oxidation dye intermediate, in which the blending amount of each member as the coupler is in a range from 0.01 to 0.5% by mass. An oxidation hair dye composition containing the hair dye composition. Wherein the hair dye composition and the oxidation hair dye composition are capable of preventing a change in the color tone of the hair dyeing even during long-term storage are provided.

6 Claims, No Drawings

HAIR DYE COMPOSITION, OXIDATION HAIR DYE COMPOSITION AND METHOD FOR PREVENTION OF CHANGE IN COLOR TONE OF HAIR DYEING

BACKGROUND OF THE INVENTION

The present invention relates to a hair dye composition, an oxidation hair dye composition and a method for prevention of a change in the color tone of hair dyeing. More particularly, the present invention relates to a hair dye composition and an oxidation hair dye composition capable of favorably preventing a change in the color tone of hair dyeing even if they are stored for a long period of time, and a method for prevention of a change in the color tone of hair dyeing achieved by these compositions.

BACKGROUND ART

An oxidation hair dye composition is generally a two-agent type which is applied to hair by mixing at the time of use. A hair dye composition as a first agent of the oxidation hair dye composition contains an oxidation dye intermediate composed of a major intermediate and a coupler, and an alkaline chemical for improving the permeability of the oxidation dye intermediate into hair as main components. A second agent contains an oxidizing agent for allowing the oxidation dye intermediate to develop a color as a main component. Such an oxidation hair dye composition is stored in a state where the first agent and the second agent are not mixed during a period until it is used.

Conventionally, a decrease in the hair-dyeing power through storage period due to oxidation of the oxidation dye intermediate during a storage period of the hair dye composition was sometimes considered as a problem. The phrase "a decrease in the hair-dyeing power" means, in short, a decrease in the depth of the color of hair dyeing. It is known that an antioxidant is blended in the first agent (hair dye composition) for preventing such a decrease in the hair-dyeing power.

For example, JP-A-2002-201117 discloses a technique in which ascorbic acid (and a nitrite salt) is blended as an antioxidant for preventing a decrease in the hair-dyeing power of an oxidation hair dye composition. However, in the case of taking measures by blending of ascorbic acid, it is known that there is a problem that a decrease in the hair-dyeing power due to long-term storage cannot be effectively prevented.

Further, JP-A-2005-41820 discloses a hair dye composition in which an ascorbic acid as a component (A) and a cysteine, cysteamine, methaphosphoric acid or the like as a component (B) are blended with respect to the blending of an antioxidant in the hair dye composition. However, the object of the invention resides in the "prevention of a change in the color of the hair dye composition itself during storage" and an object of "prevention of a decrease in the hair-dyeing power" is not presented.

As described above, prior arts in which an antioxidant is blended by focusing on an antioxidant power for coping with a problem of oxidation of an oxidation dye intermediate during storage of a hair dye composition are found.

However, an essentially important object for preventing a change in the hair dye function of a hair dye composition during a storage period is to prevent a change in the color tone which can be recognized by the naked eye. Moreover, considering that the storage period of a hair dye composition is long in many cases, it is essentially important to prevent such a change in the color tone of hair dyeing for a long period of time.

JP-A-2007-8892 has its object to prevent a change over time in the dyeing effect of a hair dye composition. The phrase "a change in the dyeing effect" as used here means "a change in the color tone of hair dyeing" as can be seen from the evaluation items in Examples. However, the means for achieving the object is to provide a three-agent type hair dye composition by separating an alkaline chemical and an oxidation dye from each other.

As described above, an object of prevention of a change in the color tone of hair dyeing during a storage period of a hair dye composition for a long period of time and means for achieving the object have not conventionally been proposed yet. The inventions described in the document 1 and document 2 cannot achieve this object. The invention described in the document 3 has a possibility to be a means for achieving the object in the end, however, it requires a configuration of three-agent type, which is not common.

SUMMARY OF THE INVENTION

An object of the present invention is to prevent a change in the color tone of hair dyeing during a storage period of a hair dye composition. The inventors of this application found that this object can be achieved only when a specific type of coupler and a specific type of antioxidant are blended in combination in a hair dye composition and the blending amount of the coupler is limited to a given level or less, and thus the present invention has been completed.

A first invention of this application is a hair dye composition comprising an alkaline chemical and an oxidation dye intermediate composed of a major intermediate and a coupler wherein at least one member selected from (1) organic compounds having not more than 4 carbon atoms, which has both of a —SH group and a —NH$_2$ group and does not have a —COOH group and (2) salts thereof is contained as a component (A), and at least one member selected from aromatic compounds in which the same or different substituents arbitrarily selected from the groups represented by the following chemical formula 1 and chemical formula 2 are each attached to meta positions of a mononuclear benzene ring structure (these aromatic compounds are also referred to as "specific meta couplers") and α-naphthol is contained as a component (B) which is the coupler, and the blending amount of each member of the component (B) is in a range from 0.01 to 0.5% by mass.

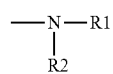
[Chemical formula 1]

(In the chemical formula 1, R1 and R2 are each arbitrarily selected from hydrogen, hydrocarbon groups having not more than 2 carbon atoms, and aliphatic alcohol groups having not more than 2 carbon atoms or salts thereof and R1 and R2 are the same or different groups from each other.)

[Chemical formula 2]

(In the chemical formula 2, R is arbitrarily selected from hydrogen, hydrocarbon groups having not more than 2 carbon atoms, and alcohol groups having not more than 2 carbon atoms or salts thereof.)

When the hair dye composition of the first invention is used, the color tone of hair dyeing is not changed even after long-term storage compared with the use thereof in the early stage of storage.

In the case where the component (A) and the component (B) are not blended in combination in the hair dye composition, a change over time in the color tone of hair dyeing during a storage period cannot be effectively prevented.

When the blending amount of each member of the component (B) is less than 0.01% by mass, a sufficient hair dye effect cannot be obtained due to a shortage of the absolute amount thereof. When the blending amount of each member of the component (B) exceeds 0.5% by mass, the effect of the present invention cannot be perceived by the naked eye even if the effect is exhibited because this is originally in a range of deep color tone in which even the color tone of hair dyeing is changed, the change is difficult to perceive by the naked eye.

In the invention described in the document 2, the blending of a meta coupler similar to that of the first invention and the blending of cysteamine belonging to the component (A) are disclosed. However, the invention described in the document 2 presents an object different from that of the present invention and further, the blending of an ascorbic acid is essential in the invention described in the document 2. Further, although the blending of a meta coupler in an amount of 0.5% by mass or less is not excluded, only Examples and Comparative examples relating to hair dye compositions in which the blending amount of a meta coupler is 1% by mass were verified. Accordingly, the invention described in the document 2 does not disclose or suggest the object and configuration of the first invention.

In a second invention of this application, the component (A) of the hair dye composition according to the first invention is at least one member selected from cysteamine and salts thereof.

The component (A) of the hair dye composition is not limited, however, at least one member selected from cysteamine and salts thereof defined in the second invention can be preferably exemplified.

In a third invention of this application, the specific meta coupler of the hair dye composition according to the first invention or the second invention is at least one member selected from resorcin, meta-aminophenol, 5-amino-o-cresol, 5-(2-hydroxyethylamino)-2-methylphenol, and salts thereof.

The specific meta coupler (that is, an aromatic compound in which the same or different substituents arbitrarily selected from the groups represented by the above-mentioned chemical formula 1 and chemical formula 2 are each attached to meta positions of a mononuclear benzene ring structure) of the component (B) of the hair dye composition is not limited, however, at least one member of the compounds listed in the third invention can be preferably exemplified.

In a fourth invention of this application, the alkalinity of the hair dye composition according to any one of the first invention to the third invention defined by the amount of consumption of 0.1 N standard acid solution is 6.0 ml/g or more.

The alkalinity of the hair dye composition is preferably 6.0 ml/g or more. When the alkalinity is less than 6.0 ml/g, a sufficient hair-dyeing power may not be obtained.

A fifth invention of this application is an oxidation hair dye composition comprising at least a first agent which is the hair dye composition according to any one of the first invention to the fourth invention, and a second agent which is an oxidizing agent composition containing an oxidizing agent and to be mixed with the hair dye composition at the time of use.

The oxidation hair dye composition according to the fifth invention contains at least the above-mentioned first agent and second agent, however, it is not necessarily a two-agent type, and can be configured as a three-agent type by adding a third agent having a preferred composition as described later.

In the oxidation hair dye composition according to the fifth invention, an effect according to the above-mentioned first invention to fourth invention can be secured when the first agent and the second agent are mixed and used.

A sixth invention of this application is a method for prevention of a change in the color tone of hair dyeing comprising incorporating a component (A) defined in the first invention in a hair dye composition containing an alkaline chemical and an oxidation dye intermediate composed of a major intermediate and a coupler and containing a component (B) defined in the first invention as the coupler, thereby preventing a change over time in the color tone of hair dyeing with a hair dye composition.

According to the sixth invention, for the above-mentioned reason with respect to the first invention, a change over time in the color tone of hair dyeing with a hair dye composition during a storage period or the like can be favorably prevented.

According to the present invention, with a hair dye composition and an oxidation hair dye composition, a change over time in the color tone of hair dyeing during a long-term storage period can be effectively prevented.

DETAILED DESCRIPTION OF THE INVENTION

Hereinafter, an embodiment for carrying out the present invention including a best mode will be described.

[Oxidation Hair Dye Composition]

An oxidation hair dye composition according to the present invention comprises at least a hair dye composition (first agent), which will be described later and an oxidizing agent composition (second agent) containing an oxidizing agent and to be mixed with the hair dye composition at the time of use.

This oxidation hair dye composition may be configured as a two-agent type comprising the above-mentioned hair dye composition (first agent) and oxidizing agent composition (second agent), or may be configured as a three-agent type by further adding a third agent to these two agents. As the third agent, a hair treatment and a conditioner having an arbitrary composition, and the like can be exemplified. These two-agent type or three-agent type oxidation hair dye compositions is used by mixing these agents at the time of use.

The formulation of the hair dye composition (first agent) or the oxidizing agent composition (second agent) which constitutes the oxidation hair dye composition or the above-mentioned third agent can be arbitrarily selected from various known formulations according to the intended application, purpose or the like. Examples thereof include liquid, emulsion, cream, gel, paste, mist (spray) and aerosol form.

[Oxidizing Agent Composition]

The oxidizing agent composition as the second agent is not limited in terms of its composition as long as it contains an oxidizing agent. In the oxidizing agent composition, in addition to an oxidizing agent, an arbitrary necessary or useful component can be incorporated.

The type of oxidizing agent to be incorporated in the oxidizing agent composition is not particularly limited and can be arbitrarily selected from various known oxidizing agents to be used for this purpose. As the oxidizing agent, hydrogen peroxide is generally used, however, other than this, potassium bromate, sodium bromate, sodium perborate, a peroxide and the like can be exemplified. The blending amount of the oxidizing agent in the oxidizing agent composition is not particularly limited, and may be suitably determined according to the intended purpose or formulation of the oxidizing agent composition or the like.

[Hair Dye Composition and Major Component Thereof]

The hair dye composition according to the present invention is mixed with the above-mentioned oxidizing agent composition (second agent) and optionally further with the third agent at the time of use. The hair dye composition contains at least an oxidation dye intermediate composed of a major intermediate and a coupler as a component (B) (at least one member selected from specific meta couplers and α-naphthol), an alkaline chemical and a component (A) described above with respect to the first invention. The blending amount of the coupler is in a range from 0.01 to 0.5% by mass for each member of the component (B).

Further, it is more preferred that the ratio of the blending amounts between the component (A) and the component (B) ((B)/(A)) is in a range from 0.01 to 2 for each member of the component (B). When the value of (B)/(A) is lower than the above range, a hair-dyeing power may tend to be lacking, and when the value of (B)/(A) is higher than the above range, the effect of the present invention may be insufficient.

In addition, it is more preferred that the hair dye composition further contains a hydrosulfite salt as a component (C). When the hair dye composition further contains a hydrosulfite salt, the effect of the present invention is further improved.

The pH of the hair dye composition is not particularly limited, however, it is preferred that the pH is generally about 7 to 12. For adjusting the pH of the hair dye composition, a suitable pH buffering component can be blended.

(Alkaline Chemical)

The type of alkaline chemical to be incorporated in the hair dye composition is not limited, however, for example, ammonia, an alkanolamine (such as monoethanolamine, diethanolamine, triethanolamine, monoisopropanolamine, diisopropanolamine, or triisopropanolamine), an ammonium salt, an organic amine (such as 2-amino-2-methyl-1-propanol, 2-amino-2-methyl-1,3-propanediol, or guanidine), an inorganic alkali (such as sodium hydroxide, potassium hydroxide, sodium carbonate, or potassium carbonate), a basic amino acid (such as arginine or lysine) or a salt thereof is suitably selected and can be used. In particular, when an organic alkali is incorporated, the effect of the present invention is easily obtained.

The content of the alkaline chemical in the hair dye composition is not necessarily limited, however, for the above-mentioned reason with respect to the fifth invention, the alkalinity of the hair dye composition is preferably 6.0 ml/g or more, and particularly preferably 8.0 ml/g or more.

(Major Intermediate)

The major intermediate in the oxidation dye intermediate is not particularly limited, however, one or more members of phenylenediamines, aminophenols, diaminopyridines and salts such as hydrochlorides, sulfates, and acetates of these compounds can be exemplified. Specifically, p-phenylenediamine, toluene-2,5-diamine, N,N-bis(β-hydroxyethyl)-p-phenylenediamine, 2-β-hydroxyethyl)-p-phenylenediamine, N-β-hydroxyethyl)-N-ethyl-p-phenylenediamine, N-phenyl-p-phenylenediamine, 4,4'-diaminodiphenylamine, 2-chloro-p-phenylenediamine, N,N-dimethyl-p-phenylenediamine, p-aminophenol, o-aminophenol, p-methylaminophenol, 2,6-dichloro-p-phenylenediamine, p-aminophenylsulfamic acid, 2,5-diaminopyridine, and salts thereof can be exemplified. The blending amount of the major intermediate is not particularly limited and may be suitably determined according to the intended depth of the color of hair dyeing.

(Coupler)

In the hair dye composition according to the present invention, at least one member selected from specific meta couplers and α-naphthol is used as the coupler, that is, as the component (B) in the oxidation dye intermediate. The term "specific meta coupler" refers to an aromatic compound in which the same or different two substituents arbitrarily selected from the groups represented by the above-mentioned chemical formula 1 and chemical formula 2 are each attached to meta positions of a mononuclear benzene ring structure.

The type of the specific meta coupler is not limited as long as it satisfies the above definition, however, as a preferred specific example, at least one member selected from resorcin, m-aminophenol, 5-amino-o-cresol, 5-(2-hydroxyethylamino)-2-methylphenol, and salts thereof can be exemplified.

The blending amount of the component (B) in the hair dye composition is, as described above, in a range from 0.01 to 0.5% by mass for each member of the component (B) in the case where one or more members is/are blended as the component (B). From the viewpoint that an effect of preventing a change in the color tone of hair dyeing with a hair dye composition after short-term to long-term storage is easily obtained, the blending amount of each member is particularly preferably in a range from 0.01 to 0.3% by mass.

(Component (A))

The component (A) refers to at least one member selected from (1) organic compounds having not more than 4 carbon atoms, which have both of a —SH group and a —NH$_2$ group and do not have a —COOH group and (2) salts thereof. As such a component (A), at least one member selected from cysteamine and salts thereof can be particularly preferably exemplified.

(Component (C))

A hydrosulfite salt as the component (C) is preferably incorporated in the hair dye composition for the above-mentioned reason. As the hydrosulfite salt, for example, a sodium salt, a potassium salt and the like can be preferably exemplified. The content of the hydrosulfite salt is not limited, however, for example, it can be set to about 0.01 to 1.0% by mass.

[Other Components in Hair Dye Composition]

In the hair dye composition, in addition to the above-mentioned various components, a vitamin, an oily component, a surfactant, a polymeric substance, a polypeptide, a protein hydrolysate, an amino acid, a sequestrant, an antioxidant, a fragrance, a disinfectant antiseptic, an antiinflammatory agent, an ultraviolet absorber, a propellant, a thickener, a colorant or the like can be arbitrarily blended as needed. As these components to be blended, any of various well-known or publicly-known substances can be arbitrarily used. Further, water is blended therein as a solvent or a dispersion medium for the respective components of the hair dye composition, and the concentrations (% by mass) of the respective components are adjusted. Some of these components to be blended will be described in detail below.

(Vitamins)

In the hair dye composition, one or more members of various vitamins can be blended in an arbitrary blending amount range. The type of vitamin is not limited, and for example, an oil-soluble or water-soluble vitamin such as an ascorbic acid or a tocopherol is arbitrarily selected and can be used.

(Oily Component)

Examples of the oily component include hydrocarbons, polyhydric alcohols, waxes, oils and fats, higher alcohols, higher fatty acids, alkyl glyceryl ethers, esters, and silicones. These can be blended alone or in combination of two or more members.

Examples of the hydrocarbon include paraffin, polyethylene powder, microcrystalline wax, and petrolatum. Further, examples of the hydrocarbon in a liquid state at room temperature include α-olefin oligomers, light isoparaffin, light liquid isoparaffin, synthetic squalane, vegetable squalane, squalane, polybutene, liquid isoparaffin, and liquid paraffin.

Examples of the polyhydric alcohol include glycols and glycerins. Examples of the glycol include ethylene glycol diethylene glycol, triethylene glycol, propylene glycol, dipropylene glycol, isoprene glycol, and 1,3-butylene glycol. Examples of the glycerin include glycerin, diglycerin, and polyglycerin.

Examples of the wax include bees wax, candelilla wax, carnauba wax, jojoba oil, lanolin, whale wax, rice bran wax, sugarcane wax, palm wax, montan wax, cotton wax, bayberry wax, ibota wax, kapok wax, and shellac wax.

Examples of the oil and fat include various vegetable oils and animal oils except for oils and fats which are polyhydric alcohol fatty acid esters.

Examples of the higher alcohol include lauryl alcohol, myristyl alcohol, cetyl alcohol (cetanol), stearyl alcohol, cetostearyl alcohol, arachyl alcohol, behenyl alcohol, 2-hexyl decanol, isostearyl alcohol, 2-octyldodecanol, decyltetradecanol, oleyl alcohol, linoleyl alcohol, linolenyl alcohol, and lanolin alcohol.

Examples of the higher fatty acid include lauric acid, myristic acid, palmitic acid, stearic acid, behenic acid, isostearic acid, hydroxystearic acid, 12-hydroxystearic acid, oleic acid, undecylenic acid, linoleic acid, ricinoleic acid, and lanolin acid fatty acids.

Examples of the alkyl glyceryl ether include batyl alcohol (monostearyl glyceryl ether), chimyl alcohol (monocetyl glyceryl ether), selachyl alcohol (monooleyl glyceryl ether), and isostearyl glyceryl ether.

Examples of the ester include various glycerin vegetable oils such as soybean oil, olive oil and hydrogenated castor oil, polyhydric alcohol fatty acid esters such as pentaerythritol fatty acid esters, diisopropyl adipate, diisobutyl adipate, dioctyl adipate, 2-hexyldecyl adipate, diisostearyl adipate, isopropyl myristate, cetyl octanoate, cetyl isooctanoate, isononyl isononanoate, isodecyl isononanoate, isotridecyl isononanoate, diisopropyl sebacate, octyldodecyl myristate, isopropyl palmitate, butyl stearate, stearyl stearate, hexyl laurate, myristyl myristate, decyl oleate, hexyldecyl dimethyl octanoate, triisodecyl myristate, isostearyl myristate, 2-ethylhexyl palmitate, octyldodecyl ricinoleate, fatty acid (C10-30) cholesteryl/lanosteryl esters, lauryl lactate, cetyl lactate, myristyl lactate, octyldodecyl lactate, lanolin acetate, isocetyl stearate, isocetyl isostearate, cholesteryl 12-hydroxystearate, ethylene glycol di-2-ethylhexanoate, dipentaerythritol fatty acid esters, N-alkyl glycol monoisostearate, cetyl caprate, glyceryl tricaprylate, neopentyl glycol dicaprate, diisostearyl malate, and lanolin derivatives.

Examples of the silicone include methylpolysiloxane, dimethylpolysiloxane, methylphenylpolysiloxane, decamethylcyclopentasiloxane, dodecamethylcyclohexasiloxane, highly polymerized silicones having an average degree of polymerization of 650 to 10000, amino-modified silicones, polyether-modified silicones, betaine-modified silicones, alkyl-modified silicones, alkoxy-modified silicones, mercapto-modified silicones, carboxy-modified silicones, trimethylsiloxysilicate, and methylhydrogen polysiloxane. Examples of the amino-modified silicone include aminopropylmethylsiloxane-dimethylsiloxane copolymers (aminopropyl dimethicone), aminoethylaminopropylsiloxane-dimethylsiloxane copolymers (amodimethicone), and aminoethylaminopropylmethylsiloxane-dimethylsiloxane copolymers (trimethylsilylamodimethicone).

(Surfactant)

Examples of the surfactant include cationic surfactants, nonionic surfactants, anionic surfactants and amphoteric surfactants other than the above-mentioned hydrogenated castor oil fatty acid ester derivatives. These can be blended alone or in combination of two or more members.

Examples of the cationic surfactant include lauryl trimethyl ammonium chloride, cetyl trimethyl ammonium chloride, stearyl trimethyl ammonium chloride, distearyl dimethyl ammonium chloride, behenyl trimethyl ammonium methyl sulfate, tri(polyoxyethylene)stearyl ammonium chloride, Quatanium-91 (INCI name), behenyl trimethyl ammonium chloride, lanolin fatty acid amidopropyl ethyl dimethyl ammonium ethylsulfate, cetyl trimethyl ammonium bromide, stearyl trimethyl ammonium bromide, stearyl trimethyl ammonium saccharin, cetyl trimethyl ammonium saccharin, and N,N-di(acyloxy), N-(hydroxyethyl), N-methyl ammonium methosulfate.

Examples of the nonionic surfactant include polyoxyethylene (hereinafter referred to as POE) alkyl ethers, POE alkyl phenyl ethers, POE polyoxypropylene alkyl ethers, POE sorbitan fatty acid esters, POE propylene glycol fatty acid esters, and aliphatic alkanol amides.

Examples of the anionic surfactant include alkyl sulfates such as sodium lauryl sulfate, POE alkyl sulfates such as POE sodium lauryl ether sulfate, alkyl sulfate ester salts such as triethanolamine lauryl sulfate, sodium stearoyl methyl taurine, triethanolamine dodecylbenzene sulfonate, sodium tetradecene sulfonate, POE lauryl ether phosphate and salts thereof, N-lauroyl glutamate, and N-lauroyl methyl-β-alanine salts.

Examples of the amphoteric surfactant include sodium 2-undecyl-N-carboxymethyl-N-hydroxyethyl imidazolinium betaine, cocoamidopropyl betaine, and lauryl dimethylamino acetic acid betaine.

(Polymeric Substance)

Examples of the polymeric substance include cationic polymers, anionic polymers such as carboxyvinyl polymer, amphoteric polymers such as diallyl quaternary ammonium salt/acrylic acid copolymers, and various water-soluble polymers. These can be blended alone or in combination of two or more members.

Specific examples of the water-soluble polymer include vegetable polymers such as gum arabic, xanthan gum, carrageenan, pectin, agar, and starch; microbial polymers such as dextran and pullulan; animal polymers such as collagen, casein, and gelatin; and cellulosic polymers such as methyl cellulose and hydroxyethyl cellulose; and other than these, sodium alginate, carboxyvinyl polymer, polyoxyethylene polymer, sodium polyacrylate, and polyacrylamide polydimethyl methylene piperidinium chloride.

(Polypeptide, Protein Hydrolysate, and Amino Acid)

Examples of the polypeptide include proteins such as collagen, keratin, elastin, fibroin, egg, silk, conchiolin, casein, and gelatin; and proteins obtained from plants such as rice, wheat, barley, oat, soybean, pea, almond, Brazil nut, potato, and corn. Examples of the protein hydrolysate include protein hydrolysates obtained by hydrolyzation of any of the above-mentioned various proteins with an acid, an alkali, an enzyme, or the like. Examples of the amino acid include various acidic amino acids, neutral amino acids, and basic amino acids.

[Method for Prevention of Change in Color Tone of Hair Dyeing]

The method for prevention of a change in the color tone of hair dyeing according to the present invention is a method for preventing a change over time in the color tone of hair dyeing with a hair dye composition containing an alkaline chemical and an oxidation dye intermediate composed of a major intermediate and a coupler and containing the above-mentioned component (B) as the coupler, and is characterized by comprising incorporating the above-mentioned component (A) in the hair dye composition.

As a subject to which this method for prevention of a change in the color tone of hair dyeing can be applied, the above-mentioned hair dye composition, or a two-agent type or three-agent type oxidation hair dye composition containing this hair dye composition as the first agent can be exemplified.

The contents of the major intermediate and alkaline chemical in the above-mentioned hair dye composition are the same as described above. A more preferred blending amounts of the component (B) and the component (A) are the same as described above. When the component (C) is blended in the hair dye composition in addition to the component (B) and the component (A), the effect is further improved. In the hair dye composition, any of various components described in the item of "Other components in hair dye composition" described above can be blended as needed.

EXAMPLES

Hereinafter, the present invention will be described together with Examples and Comparative examples. The technical scope of the present invention is not limited to these Examples and Comparative examples.

Examples and Comparative Examples According to First Example Group

Hair dye compositions in a cream form having any of the compositions according to Example 1 to Example 15 shown in Table 1 at the end and Comparative example 1 to Comparative example 13 shown in Table 2 at the end were prepared in accordance with a common procedure. Incidentally, as can be seen from the compositions, Example 15, Comparative example 12 and Comparative example 13 are blending examples with which hair is dyed a deep color. All of these hair dye compositions are used as a first agent of an oxidation hair dye, and an oxidation hair dye is prepared by mixing any of the hair dye compositions with an oxidizing agent composition in a cream form having the following composition as a second agent of the oxidation hair dye at the time of use. (Second agent)

| 35% Hydrogen peroxide solution | 17.0% by mass |
| Sodium stannate | 0.1% by mass |
| EDTA | 0.5% by mass |
| Cetanol | 2.0% by mass |
| Sodium lauryl sulfate | 1.0% by mass |
| Phosphoric acid | 0.5% by mass |
| Purified water | Residual quantity |

Incidentally, regard to the respective components shown in Table 1 and Table 2, when the component serves as the component (A), the component (B) or the component (C), the indication is made in the margin. Further, all the numerical values indicating the amounts of the components shown in Table 1 and Table 2 are represented in a unit of % by mass. Further, the alkalinities (ml/g) of the respective hair dye compositions defined by the amount of consumption of 0.1 N standard acid solution are also shown in the tables.

[Evaluation of Examples and Comparative Examples]
(Evaluation 1: Cloth Dyeing Test)

An oxidation hair dye was prepared by mixing each of the hair dye compositions according to Examples and Comparative examples shown in Table 1 and Table 2 with the above-mentioned oxidizing agent composition at a mass ratio of 1:1. Then, each of the (1) oxidation hair dye immediately after the preparation and the (2) oxidation hair dye after it was stored at 60° C. for 2 weeks after the preparation was applied to a white test cloth (JIS L0803 attached white cloth for the dye color fastness test), and the test cloth was left as such for 20 minutes. Then, the test cloth was washed with water and dried, whereby a dyed cloth was obtained. Incidentally, the condition of "storage at 60° C. for 2 weeks" of the oxidation hair dye corresponds to storage at room temperature for 3 years.

The values in L*a*b* color system (CIE 1976) were measured for the cloths dyed with the above-mentioned oxidation hair dyes (1) and (2) according to the respective Examples and Comparative examples using a spectrocolorimeter (manufactured by Konica Minolta Co., Ltd., CM-508d). For the respective examples, the a*b* values ($a_0$, $b_0$) of the cloth dyed with the oxidation hair dye immediately after the preparation, and the a*b* values ($a_1$, $b_1$) of the cloth dyed with the oxidation hair dye after it was stored at 60° C. for 2 weeks were measured, and a color difference ΔE(a, b) was calculated according to the following equation 1. The calculated value is shown in the line of "ΔE(a, b) 60° C.·2W" of Tables 1 and 2.

$$\Delta E(a,b) = \{(a_1-a_0)^2 + (b_1-b_0)^2\}^{1/2} \qquad \text{Equation 1}$$

The case where the calculated ΔE(a, b) is 0 or more and less than 0.5 is assigned to "◯◯"; the case where the calculated ΔE(a, b) is 0.5 or more and less than 1 is assigned to "◯"; the case where the calculated ΔE(a, b) is 1 or more and less than 2 is assigned to "Δ"; and the case where the calculated ΔE(a, b) is 2 or more is assigned to "x". These results are shown in the line of "evaluation of ΔE(a, b)" of Tables 1 and 2.

(Evaluation 2: Visual Evaluation of Color Difference)

An oxidation hair dye was prepared by mixing each of the hair dye compositions according to Examples and Comparative examples shown in Table 1 and Table 2 with the above-mentioned oxidizing agent composition at a mass ratio of 1:1. Then, a hair dye treatment was performed by applying each of the (1) oxidation hair dye immediately after the preparation and the (2) oxidation hair dye after it was stored at 60° C. for 2 weeks after the preparation to (a) an untreated human black hair bundle and (b) a black hair bundle treated with a commercially available bleach (trade name: Beautylabo Bleach S, manufactured by Hoyu Co., Ltd.) by a common procedure, and leaving the hair bundles as such for 30 minutes, and then putting a plain conditioner on the hair bundles.

Subsequently, a color difference was visually evaluated between the hair bundles subjected to the hair dye treatment with the above-mentioned oxidation hair dyes (1) and (2). This evaluation of color difference was performed separately for both of the case where the above-mentioned (a) was used and the case where the above-mentioned (b) was used. In the evaluation, the case where a color difference is not noticed is assigned to "◯"; the case where some color difference is noticed is assigned to "Δ"; and the case where an apparent color difference is noticed is assigned to "x". These results are shown in the line of "Visual evaluation of color difference" of Tables 1 and 2. Incidentally, when the evaluation results obtained in the case where (a) was used and the case where (b) was used disagreed with each other in the same Example or Comparative example, the worse evaluation result was adopted. However, in fact, in almost all the Examples and Comparative examples, the evaluation results obtained in the case where (a) was used and the case where (b) was used agreed with each other.

Examples and Comparative Examples According to Second Example Group

Hair dye compositions in a liquid form having either of the compositions according to Example 16 and Comparative example 14 shown in Table 3 at the end were prepared in accordance with a common procedure. Both of these hair dye compositions are used as a first agent of an oxidation hair dye, and an oxidation hair dye is prepared by mixing either of the hair dye composition with an oxidizing agent composition in an emulsion form having the same composition as described above in the first example group as a second agent of the oxidation hair dye.

As for the respective components shown in Table 3, when the component serves as the component (A), the component (B) or the component (C), the indication is made in the margin. All the numerical values indicating the amounts of the components shown in Table 3 are represented in a unit of % by mass. Further, the alkalinities (ml/g) of the respective hair dye compositions defined by the amount of consumption of 0.1 N standard acid solution are also shown in the table.

For the hair dye compositions according to Example 16 and Comparative example 14 shown in Table 3, in exactly the same manner as in the case of the first example group including the mixing mass ratio of the hair dye composition to the oxidizing agent composition, a cloth dyeing test was performed, the values in L*a*b* color system (CIE 1976) were measured, a color difference ΔE(a, b) was calculated according to the above-mentioned equation 1, and the calculated ΔE(a, b) was evaluated and assigned to any of "○○" to "x". These results are shown in the line of "Evaluation of ΔE(a, b)" of Table 3.

Further, for the hair dye compositions according to Example 16 and Comparative example 14, a visual evaluation of a color difference was performed in exactly the same manner as in the case of the first example group including the mixing mass ratio of the hair dye composition to the oxidizing agent composition. These results are shown in the line of "Visual evaluation of color difference" of Table 3.

TABLE 1

| | | Example | | | | | | | |
|---|---|---|---|---|---|---|---|---|---|
| | | 1 | 2 | 3 | 4 | 5 | 6 | 7 | 8 |
| A | Cysteamine hydrochloride | 0.2 | 0.5 | 0.5 | 0.5 | 0.5 | 0.3 | 0.5 | 0.5 |
| | Ascorbic acid | — | — | — | — | — | — | — | — |
| | 50% ammonium thioglycolate | — | — | — | — | — | — | — | — |
| | Cysteine | — | — | — | — | — | — | — | — |
| C | Sodium hydrosulfite | — | — | — | — | 0.1 | — | — | — |
| | p-Phenylenediamine | 0.1 | 0.1 | 0.1 | 0.1 | 0.1 | 0.1 | 0.1 | 0.1 |
| | p-Aminophenol | 0.5 | 0.5 | 0.5 | 0.5 | 0.5 | 0.5 | 0.5 | 0.5 |
| B | Resorcin | 0.5 | 0.5 | 0.3 | 0.1 | 0.3 | 0.3 | 0.3 | 0.3 |
| B | 2,4-Diaminophenoxyethanol | — | — | — | — | — | — | — | — |
| B | 5-Amino-o-cresol | — | — | — | — | — | — | — | — |
| B | m-Aminophenol | — | — | — | — | — | — | — | — |
| B | 5-(2-Hydroxyethylamino)-2-methylphenol | — | — | — | — | — | — | — | — |
| B | α-naphthol | — | — | — | — | — | — | — | — |
| | 28% Ammonia water | 2.0 | 2.0 | 2.0 | 2.0 | 2.0 | 2.0 | 1.0 | 4.0 |
| | 70% Monoethanolamine | 5.0 | 5.0 | 5.0 | 5.0 | 5.0 | 5.0 | 5.0 | — |
| | POE (5) stearyl ether | 7.0 | 7.0 | 7.0 | 7.0 | 7.0 | 7.0 | 7.0 | 7.0 |
| | POE (20) cetyl ether | 5.0 | 5.0 | 5.0 | 5.0 | 5.0 | 5.0 | 5.0 | 5.0 |
| | Sodium cetyl sulfate | 2.0 | 2.0 | 2.0 | 2.0 | 2.0 | 2.0 | 2.0 | 2.0 |
| | Stearyltrimethylammonium chloride | 2.0 | 2.0 | 2.0 | 2.0 | 2.0 | 2.0 | 2.0 | 2.0 |
| | Propylene glycol | 3.0 | 3.0 | 3.0 | 3.0 | 3.0 | 3.0 | 3.0 | 3.0 |
| | Cetanol | 5.0 | 5.0 | 5.0 | 5.0 | 5.0 | 5.0 | 5.0 | 5.0 |
| | Purified water | Residual quantity | Residual quantity | Residual quantity | Residual quantity | Residual quantity | Residual quantity | Residual quantity | Residual quantity |
| | Alkalinity of first agent (ml/g) | 9.03 | 9.03 | 9.03 | 9.03 | 9.03 | 9.03 | 7.38 | 6.58 |
| | ΔE (a, b) 60° C. · 2 W | 0.92 | 0.72 | 0.87 | 0.98 | 0.42 | 0.88 | 0.68 | 0.29 |
| | Evaluation of ΔE (a, b) | ○ | ○ | ○ | ○ | ○○ | ○ | ○ | ○○ |
| | Visual evaluation of color difference | ○ | ○ | ○ | ○ | ○ | ○ | ○ | ○ |

| | | Example | | | | | | |
|---|---|---|---|---|---|---|---|---|
| | | 9 | 10 | 11 | 12 | 13 | 14 | 15 |
| A | Cysteamine hydrochloride | 0.5 | 0.5 | 0.5 | 0.5 | 0.5 | 0.5 | 0.5 |
| | Ascorbic acid | 0.5 | — | — | — | — | — | — |
| | 50% ammonium thioglycolate | — | — | — | — | — | — | — |
| | Cysteine | — | — | — | — | — | — | — |
| C | Sodium hydrosulfite | — | — | — | — | — | — | — |
| | p-Phenylenediamine | 0.1 | 0.1 | 0.5 | 0.5 | 0.5 | 0.1 | 1.0 |
| | p-Aminophenol | 0.5 | 0.5 | — | — | — | 0.5 | — |
| B | Resorcin | 0.3 | — | — | — | — | 0.5 | — |
| B | 2,4-Diaminophenoxyethanol | — | 0.1 | — | — | 0.1 | — | — |
| B | 5-Amino-o-cresol | — | 0.3 | — | — | — | — | 0.1 |
| B | m-Aminophenol | — | — | 0.3 | — | — | — | — |
| B | 5-(2-Hydroxyethylamino)-2-methylphenol | — | — | — | 0.3 | — | — | — |
| B | α-naphthol | — | — | — | — | 0.3 | — | — |

TABLE 1-continued

|  | | | | | | | |
|---|---|---|---|---|---|---|---|
| 28% Ammonia water | 2.0 | 2.0 | 2.0 | 2.0 | 2.0 | — | 2.0 |
| 70% Monoethanolamine | 5.0 | 5.0 | 5.0 | 5.0 | 5.0 | 4.0 | 5.0 |
| POE (5) stearyl ether | 7.0 | 7.0 | 7.0 | 7.0 | 7.0 | 7.0 | 7.0 |
| POE (20) cetyl ether | 5.0 | 5.0 | 5.0 | 5.0 | 5.0 | 5.0 | 5.0 |
| Sodium cetyl sulfate | 2.0 | 2.0 | 2.0 | 2.0 | 2.0 | 2.0 | 2.0 |
| Stearyltrimethylammonium chloride | 2.0 | 2.0 | 2.0 | 2.0 | 2.0 | 2.0 | 2.0 |
| Propylene glycol | 3.0 | 3.0 | 3.0 | 3.0 | 3.0 | 3.0 | 3.0 |
| Cetanol | 5.0 | 5.0 | 5.0 | 5.0 | 5.0 | 5.0 | 5.0 |
| Purified water | Residual quantity | Residual quantity | Residual quantity | Residual quantity | Residual quantity | Residual quantity | Residual quantity |
| Alkalinity of first agent (ml/g) | 8.74 | 8.99 | 9.03 | 9.03 | 8.99 | 4.59 | 9.03 |
| Δ E (a, b) 60° C. · 2 W | 0.99 | 0.70 | 0.15 | 0.56 | 0.95 | 0.19 | 0.64 |
| Evaluation of Δ E (a, b) | ○ | ○ | ○○ | ○ | ○ | ○○ | ○ |
| Visual evaluation of color difference | ○ | ○ | ○ | ○ | ○ | ○ | ○ |

TABLE 2

| | | Comparative example | | | | | | |
|---|---|---|---|---|---|---|---|---|
| | | 1 | 2 | 3 | 4 | 5 | 6 | 7 |
| A | Cysteamine hydrochloride | — | — | — | — | — | — | — |
| | Ascorbic acid | — | 0.5 | — | — | 0.5 | 0.5 | 0.5 |
| | 50% ammonium thioglycolate | — | — | 1.0 | — | — | — | — |
| | Cysteine | — | — | — | 0.5 | — | — | — |
| C | Sodium hydrosulfite | — | — | — | — | — | — | — |
| | p-Phenylenediamine | 0.1 | 0.1 | 0.1 | 0.1 | 0.1 | 0.1 | 0.1 |
| | p-Aminophenol | 0.5 | 0.5 | 0.5 | 0.5 | 0.5 | 0.5 | 0.5 |
| B | Resorcin | 0.3 | 0.3 | 0.3 | 0.3 | — | 0.6 | 1.0 |
| B | 2,4-Diaminophenoxyethanol | — | — | — | — | — | — | — |
| B | 5-Amino-o-cresol | — | — | — | — | — | — | — |
| B | m-Aminophenol | — | — | — | — | — | — | — |
| B | 5-(2-Hydroxyethylamino)-2-methylphenol | — | — | — | — | — | — | — |
| B | α-naphthol | — | — | — | — | — | — | — |
| | p-Methylaminophenol sulfate | — | — | — | — | 0.5 | — | — |
| | 28% Ammonia water | 2.0 | 2.0 | 2.0 | 2.0 | 2.0 | 2.0 | 2.0 |
| | 70% Monoethanolamine | 5.0 | 5.0 | 5.0 | 5.0 | 5.0 | 5.0 | 5.0 |
| | POE (5) stearyl ether | 7.0 | 7.0 | 7.0 | 7.0 | 7.0 | 7.0 | 7.0 |
| | POE (20) cetyl ether | 5.0 | 5.0 | 5.0 | 5.0 | 5.0 | 5.0 | 5.0 |
| | Sodium cetyl sulfate | 2.0 | 2.0 | 2.0 | 2.0 | 2.0 | 2.0 | 2.0 |
| | Stearyltrimethylammonium chloride | 2.0 | 2.0 | 2.0 | 2.0 | 2.0 | 2.0 | 2.0 |
| | Propylene glycol | 3.0 | 3.0 | 3.0 | 3.0 | 3.0 | 3.0 | 3.0 |
| | Cetanol | 5.0 | 5.0 | 5.0 | 5.0 | 5.0 | 5.0 | 5.0 |
| | Purified water | Residual quantity | Residual quantity | Residual quantity | Residual quantity | Residual quantity | Residual quantity | Residual quantity |
| | Alkalinity of first agent (ml/g) | 9.03 | 8.74 | 9.03 | 9.03 | 8.45 | 8.74 | 8.74 |
| | Δ E (a, b) 60° C. · 2 W | 1.58 | 2.66 | 1.76 | 1.02 | 0.96 | 1.18 | 0.88 |
| | Evaluation of Δ E (a, b) | Δ | X | Δ | Δ | ○ | Δ | ○ |
| | Visual evaluation of color difference | Δ | X | Δ | Δ | ○ | ○ | ○ |

| | | Comparative example | | | | | |
|---|---|---|---|---|---|---|---|
| | | 8 | 9 | 10 | 11 | 12 | 13 |
| A | Cysteamine hydrochloride | — | — | — | 0.5 | — | — |
| | Ascorbic acid | 0.5 | 0.5 | 0.5 | — | 0.5 | — |
| | 50% ammonium thioglycolate | — | — | — | — | — | — |
| | Cysteine | — | — | — | — | — | — |
| C | Sodium hydrosulfite | — | — | — | — | — | — |
| | p-Phenylenediamine | 0.1 | 0.1 | 0.1 | 0.1 | 1.0 | 1.0 |
| | p-Aminophenol | 0.5 | 0.5 | 0.5 | 0.5 | — | — |
| B | Resorcin | — | — | — | — | — | — |
| B | 2,4-Diaminophenoxyethanol | 0.1 | 0.1 | 0.1 | 0.1 | — | — |
| B | 5-Amino-o-cresol | 0.3 | 0.6 | 1.0 | 0.6 | 0.1 | 0.1 |
| B | m-Aminophenol | — | — | — | — | — | — |
| B | 5-(2-Hydroxyethylamino)-2-methylphenol | — | — | — | — | — | — |
| B | α-naphthol | — | — | — | — | — | — |
| | p-Methylaminophenol sulfate | — | — | — | — | — | — |
| | 28% Ammonia water | 2.0 | 2.0 | 2.0 | 2.0 | 2.0 | 2.0 |
| | 70% Monoethanolamine | 5.0 | 5.0 | 5.0 | 5.0 | 5.0 | 5.0 |
| | POE (5) stearyl ether | 7.0 | 7.0 | 7.0 | 7.0 | 7.0 | 7.0 |
| | POE (20) cetyl ether | 5.0 | 5.0 | 5.0 | 5.0 | 5.0 | 5.0 |
| | Sodium cetyl sulfate | 2.0 | 2.0 | 2.0 | 2.0 | 2.0 | 2.0 |
| | Stearyltrimethylammonium chloride | 2.0 | 2.0 | 2.0 | 2.0 | 2.0 | 2.0 |
| | Propylene glycol | 3.0 | 3.0 | 3.0 | 3.0 | 3.0 | 3.0 |
| | Cetanol | 5.0 | 5.0 | 5.0 | 5.0 | 5.0 | 5.0 |

TABLE 2-continued

| Purified water | Residual quantity | Residual quantity | Residual quantity | Residual quantity | Residual quantity | Residual quantity |
| --- | --- | --- | --- | --- | --- | --- |
| Alkalinity of first agent (ml/g) | 8.70 | 8.70 | 8.70 | 8.99 | 8.74 | 9.03 |
| Δ E (a, b) 60° C. · 2 W | 2.61 | 1.28 | 0.76 | 0.58 | 2.95 | 1.20 |
| Evaluation of Δ E (a, b) | X | Δ | ○ | ○ | X | Δ |
| Visual evaluation of color difference | X | ○ | ○ | ○ | X | Δ |

TABLE 3

| | | Example 16 | Comparative example 14 |
| --- | --- | --- | --- |
| A | Cysteamine hydrochloride | 0.5 | — |
| | Ascorbic acid | — | 0.5 |
| | 50% ammonium thioglycolate | — | — |
| | Cysteine | — | — |
| C | Sodium hydrosulfite | — | — |
| | p-Phenylenediamine | 0.1 | 0.1 |
| | p-Aminophenol | 0.5 | 0.5 |
| B | Resorcin | — | — |
| B | 2,4-Diaminophenoxyethanol | — | — |
| B | 5-Amino-o-cresol | 0.1 | 0.1 |
| B | m-Aminophenol | — | — |
| B | 5-(2-Hydroxyethylamino)-2-methylphenol | — | — |
| B | α-naphthol | — | — |
| | 28% Ammonia water | 2 | 2 |
| | 70% Monoethanolamine | 5 | 5 |
| | Oleic acid | 10 | 10 |
| | POE (10) oleyl ether | 7 | 7 |
| | Isopropanol | 10 | 10 |
| | Edetate disodium | 0.2 | 0.2 |
| | Sodium sulfite | 0.5 | 0.5 |
| | Purified water | Residual quantity | Residual quantity |
| | Alkalinity of first agent (ml/g) | 9.03 | 8.74 |
| | ΔE (a, b) 60° C. · 2W | 0.97 | 1.68 |
| | Evaluation of ΔE (a, b) | ○ | Δ |
| | Visual evaluation of color difference | ○ | Δ |

According to the present invention, a hair dye composition and an oxidation hair dye composition capable of effectively preventing a change in the color tone of hair dyeing even during long-term storage are provided.

The invention claimed is:

1. A hair dye composition comprising an alkaline chemical and an oxidation dye intermediate composed of a major intermediate and a coupler, wherein at least one member selected from (1) organic compounds having not more than 4 carbon atoms, which has both of a —SH group and a —NH₂ group and does not have a —COOH group and (2) salts thereof is contained as a component (A), and at least one member selected from aromatic compounds which are specific meta couplers in which the same or different substituents arbitrarily selected from the groups represented by the following chemical formula 1 and chemical formula 2 are each attached to meta positions of a mononuclear benzene ring structure and α-naphthol is contained as a component (B) which is the coupler, and the blending amount of each member of the component (B) is in a range from 0.01 to 0.5% by mass:

[Chemical formula 1]

wherein R1 and R2 are each arbitrarily selected from hydrogen, hydrocarbon groups having not more than 2 carbon atoms, and aliphatic alcohol groups having not more than 2 carbon atoms or salts thereof and R1 and R2 are the same or different groups from each other; and

[Chemical formula 2]

wherein R is arbitrarily selected from hydrogen, hydrocarbon groups having not more than 2 carbon atoms, and alcohol groups having not more than 2 carbon atoms or salts thereof.

2. The hair dye composition according to claim 1, wherein the component (A) of the hair dye composition is at least one member selected from cysteamine and salts thereof.

3. The hair dye composition according to claim 1, wherein the specific meta coupler of the hair dye composition is at least one member selected from resorcin, meta-aminophenol, 5-amino-o-cresol, 5-(2-hydroxyethylamino)-2-methylphenol, and salts thereof.

4. The hair dye composition according to claim 1, wherein the alkalinity of the hair dye composition defined by the amount of consumption of 0.1 N standard acid solution is 6.0 ml/g or more.

5. An oxidation hair dye composition comprising at least a first agent which is the hair dye composition according to claim 1, and a second agent which is an oxidizing agent composition containing an oxidizing agent and to be mixed with the hair dye composition at the time of use.

6. A method for prevention of a change in the color tone of hair dyeing comprising incorporating a component (A) according to claim 1 in a hair dye composition containing an alkaline chemical and an oxidation dye intermediate composed of a major intermediate and a coupler and containing a component (B) according to claim 1 as the coupler, thereby preventing a change over time in the color tone of hair dyeing with a hair dye composition.

* * * * *

UNITED STATES PATENT AND TRADEMARK OFFICE
CERTIFICATE OF CORRECTION

PATENT NO. : 8,202,326 B2
APPLICATION NO. : 13/145021
DATED : June 19, 2012
INVENTOR(S) : Masao Ito et al.

It is certified that error appears in the above-identified patent and that said Letters Patent is hereby corrected as shown below:

On the Title page from:   (75) "Hisohisa Murakoshi, Aichi-gun (JP)"

to:     (75) --Hirohisa Murakoshi, Aichi-gun (JP)--

Signed and Sealed this
Twenty-eighth Day of August, 2012

David J. Kappos
*Director of the United States Patent and Trademark Office*